United States Patent
Feugnet et al.

(10) Patent No.: US 8,968,554 B2
(45) Date of Patent: Mar. 3, 2015

(54) PROCESS FOR THE PRODUCTION OF MIDDLE DISTILLATE FROM A CONVENTIONAL HEAVY FEEDSTOCK INCLUDING A STEP FOR SELECTIVE HYDROGENATION OF THE EX FCC HCO CUT

(71) Applicant: IFP Energies nouvelles, Rueil-Malmaison Cedex (FR)

(72) Inventors: Frederic Feugnet, Lyons (FR); Damien Hudebine, Lyons (FR); Romain Roux, Rueil Malmaison (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 0 days.

(21) Appl. No.: 13/683,134

(22) Filed: Nov. 21, 2012

(65) Prior Publication Data
US 2013/0137907 A1    May 30, 2013

(30) Foreign Application Priority Data
Nov. 24, 2011 (FR) .................................... 11 03592

(51) Int. Cl.
| C10G 57/00 | (2006.01) |
| C07C 4/06 | (2006.01) |
| C10G 45/50 | (2006.01) |
| C10G 50/00 | (2006.01) |
| C10G 67/06 | (2006.01) |
| C10G 69/04 | (2006.01) |
| C10G 69/12 | (2006.01) |
| C10G 11/18 | (2006.01) |

(52) U.S. Cl.
CPC . *C07C 4/06* (2013.01); *C10G 45/50* (2013.01); *C10G 50/00* (2013.01); *C10G 67/06* (2013.01); *C10G 69/04* (2013.01); *C10G 69/126* (2013.01); *C10G 11/18* (2013.01)
USPC ............................................................ 208/67

(58) Field of Classification Search
USPC ......................................... 208/113, 46, 49, 67
See application file for complete search history.

(56) References Cited

U.S. PATENT DOCUMENTS

| 5,152,883 | A | 10/1992 | Melin et al. | |
| 6,207,041 | B1 * | 3/2001 | Morel et al. | 208/89 |
| 6,656,346 | B2 * | 12/2003 | Ino et al. | 208/120.01 |
| 2011/0047862 | A1 * | 3/2011 | Mayeur et al. | 44/307 |
| 2011/0073523 | A1 * | 3/2011 | Cui et al. | 208/68 |

FOREIGN PATENT DOCUMENTS

| EP | 0 432 235 A1 | 6/1991 |
| EP | 1 050 572 A2 | 11/2000 |
| FR | 2 769 635 A1 | 4/1999 |
| WO | 90/15121 A1 | 12/1990 |

OTHER PUBLICATIONS

Search Report, issued Feb. 10, 2012 in corresponding FR1103592.

* cited by examiner

*Primary Examiner* — Randy Boyer
*Assistant Examiner* — Juan Valencia
(74) *Attorney, Agent, or Firm* — Millen, White, Zelano & Branigan, P.C.

(57) ABSTRACT

The present invention describes a process for the conversion of a heavy feedstock for improving the production and selectivity for middle distillate, said process using a catalytic cracking unit followed by a unit for selective hydrogenation of the heavy distillate cut (HCO) or any other cut rich in triaromatic compounds before recycling it to the FCC reaction zone in order to maximize the middle distillate cut.

10 Claims, 1 Drawing Sheet

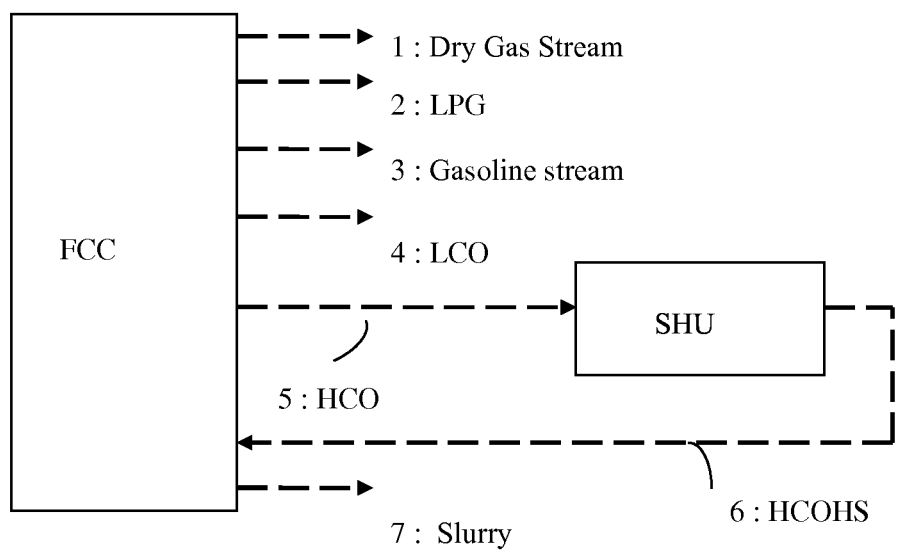

PROCESS FOR THE PRODUCTION OF MIDDLE DISTILLATE FROM A CONVENTIONAL HEAVY FEEDSTOCK INCLUDING A STEP FOR SELECTIVE HYDROGENATION OF THE EX FCC HCO CUT

FIELD OF THE INVENTION

The present invention relates to a process for the conversion of a heavy hydrocarbon feedstock with improved selectivity for middle distillate. More precisely, the process of the present invention can be used to co-produce gasoline in a reduced yield, and to improve the production of middle distillate by at least 2% by weight with respect to the feedstock, which is highly significant having regard to the tonnages involved in the process.

Historically, catalytic cracking units, known by the abbreviation FCC (fluid catalytic cracking), are optimized for the production of light products—liquefied gas (or LPG), light olefins and gasoline—in order to satisfy the polymer market or the requirements of gasoline consumption in the automobile market.

In that type of function, the production of gas oil bases remains limited.

Currently, because of huge increases in the use of diesel on the automobile market, the demand for gas oil type products has increased greatly. As a consequence, it is becoming ever more necessary to orientate refinery production towards the production of gas oil bases and to limit the production of gasoline. Since FCC units, which are present in almost half of refineries, are on the one hand the principal source of gasoline and on the other hand a major source of light olefins, it is imperative to be able to convert them into units favouring the production of gas oils. The skilled person encapsulates this trend by using the term "maxi LCO mode FCC", where LCO in this case designates the middle distillate cut, i.e. a cut with a distillation range in the range 220° C. to 360° C.

The process of the present invention can be used 1) to improve the production of gas oil bases in fluidized bed catalytic cracking units, 2) limit the production of heavy cuts that are difficult to upcycle, and also 3) limit the production of gasoline, since this cut is not wanted for maxi LCO mode running.

The present invention essentially consists of a concatenation of a FCC unit with one or more units for the selective hydrogenation of the heavy distillate cut (HCO) produced in the FCC, or any other cut which is rich in triaromatic compounds obtained, for example, from visbreaking, coking, "H-oil" units or the Pygas cut from a steam cracking unit.

This heavy distillate cut is selectively hydrotreated in order to minimize the proportion of triaromatics, while maximizing the ratio of diaromatics to monoaromatics. It is then recycled to the reaction zone of the FCC in order to significantly increase the yield of middle distillate (LCO) and also the selectivity of that cut with respect to gasoline while limiting the production of additional coke.

In the context of the present invention, the "middle distillate" cut (LCO) has a distillation range in the range 220° C. to 360° C.

The FCC process can be used to convert heavy hydrocarbon feedstocks with an initial boiling point which is generally more than 340° C. into lighter hydrocarbon fractions, in particular a gasoline cut, by cracking molecules of the heavy feedstock in the presence of an acid catalyst. FCC also produces liquefied petroleum gas (LPG) in large quantities with high olefins contents.

The process of the present invention may also generally be presented as a process for the production of middle distillate with an improvement of the selectivity for middle distillate over gasoline.

The present invention employs a catalytic cracking unit followed by one or more units for selective hydrogenation of the heavy distillate cut with a distillation range in the range 320° C. to 490° C. and primarily composed of triaromatics. This cut is usually denoted (HCO), an abbreviation which we shall retain in the text below.

The selective hydrogenation unit may also treat any other cut which is rich in triaromatic compounds obtained, for example, from visbreaking, coking, an H-oil unit or the Pygas cut from a steam cracking unit.

The process of the invention essentially consists of a concatenation of a catalytic cracking unit and one or more hydrotreatment units which selectively treat the HCO cut, with a recycle of the hydrotreated HCO cut to the catalytic cracking unit, as well as fine-tuning the hydrotreatment operating conditions in order to selectively transform the triaromatics of the feedstock for the unit into diaromatics, while maximizing the diaromatics to monoaromatics ratio. When recycled to the FCC reaction zone, the selectively hydrotreated HCO cut can be used to very significantly improve the selectivity for middle distillate of the process as well as limit the additional production of gasoline and coke.

The present invention is compatible with all catalytic cracking reactor technologies, whether it is gas-solid upflow technology or downflow technology.

The catalytic cracking unit employed in the present process may be classified into a number of modes, with a single reactor or a plurality of reactors, each reactor being able to operate in upflow or in downflow mode.

In the case of a plurality of selective hydrogenation units associated with the catalytic cracking unit, they can be arranged in series or in parallel.

EXAMINATION OF THE PRIOR ART

The prior art teaches recycling the cut known as the heavy distillate (HCO) to the reaction zone of the FCC, but not recycling said selectively hydrotreated cut with a view to maximizing middle distillate formation. One essential difference of the present invention over the prior art process cited above pertains precisely to the selective nature of the hydrogenation and to fine-tuning its operating conditions.

Patent FR 10/04 585 describes a process for the conversion of a heavy feedstock that can be used to improve the selectivity for middle distillate by using a catalytic cracking unit followed by one or more olefin oligomerization units in order to preferentially produce an additional middle distillate cut.

The present invention consists of a concatenation of a catalytic cracking unit (FCC) and one or more units for the selective hydrogenation of heavy distillate in order to significantly improve the production of middle distillate and at the same time to improve the selectivity for middle distillate over gasoline while at the same time limiting the formation of additional coke.

BRIEF DESCRIPTION OF THE FIGURE

FIG. 1 shows a layout of the process of the invention, showing the catalytic cracking unit (FCC) from which a dry gas stream 1, LPG stream 2, gasoline stream 3, LCO cut stream 4 and HCO cut stream 5 are extracted, which latter is sent to the selective hydrogenation unit (SHU). This selectively hydrogenated stream 6, denoted HCOSH, is recycled to the FCC unit (stream 6). The stream 7 represents the "slurry" cut, i.e. a 440° C.+ cut.

BRIEF DESCRIPTION OF THE INVENTION

The invention concerns a process for the conversion of a "heavy" hydrocarbon feedstock, i.e. constituted by hydrocarbons with a boiling point of more than approximately 340° C., with a view to improving the production of middle distillate and of reducing the production of gasoline.

The term "middle distillate", denoted LCO, means a cut with a distillation range in the range 220° C. to 360° C.

The term "gasoline" means the cut with a distillation range of 70° C. to 150° C.

The process of the invention comprises at least two reaction steps, a first catalytic cracking step to process a heavy hydrocarbon feedstock such as a vacuum distillate or an atmospheric residue, or even in some cases a vacuum residue, and a second step for selective hydrogenation of the heavy distillate cut resulting from FCC, denoted HCO, alone or as a mixture with any other cut which is rich in triaromatic compounds obtained, for example, from visbreaking, coking, "H-oil" type units or the Pygas cut from a steam cracking unit.

The selective nature of the hydrogenation of the heavy distillate cut (HCO) can be used to limit the formation of monoaromatics which increase production of the gasoline cut after cracking in the FCC riser, the gasoline cut not being wanted in the maxi LCO operational mode, which is precisely the mode employed in the present invention.

The transformation of triaromatics can be employed to produce diaromatics which are vital to the production of LCO, but also to limit the formation of coke, a major product of these compounds after passing through the FCC. In the end, selective hydrogenation of the heavy distillate cut (HCO) can be used to substantially improve the middle distillate (LCO) to gasoline selectivity compared with a recycle of that cut to the FCC without hydrotreatment or with conventional hydrotreatment.

In the remainder of the text, the terms "hydrotreatment" and "selective hydrogenation" should be considered to be synonymous. Thus, both "hydrotreated HCO cut" and "selectively hydrogenated HCO cut" will be employed interchangeably.

The process of the invention can be used to satisfy two objectives:
  upcycle the heavy distillate cut (HCO) or any cut which is rich in triaromatics, limiting the production of additional coke thereby;
  increase the production of middle distillate (LCO) at the same time as the middle distillate to gasoline selectivity.

The middle distillate cut (LCO) corresponds to a hydrocarbon cut with a distillation range in the range 220° C. to 360° C.

The primary aim of upgrading the heavy distillate cut (HCO) produced in the FCC or any cut which is rich in triaromatics is achieved by sending that cut to one or more hydrogenation units in order to reduce its triaromatics content, coke precursors, and heavy compounds that cannot be upgraded after recycling to the FCC reaction zone.

The second aim in improving the production of middle distillate (LCO) and the middle distillate to gasoline selectivity is obtained by fine-tuning the operating conditions for the selective hydrogenation of the ex FCC HCO cut in order to selectively transform the triaromatic compounds into diaromatics, middle distillate precursors, while minimizing the production of monoaromatics, which are gasoline precursors.

The heavy hydrocarbon feedstock is cracked in a fluidized bed catalytic cracking reactor in the presence of a cracking catalyst.

The heavy distillate cut (HCO) or any other cut which is rich in triaromatic compounds is selectively hydrotreated in the presence of a hydrotreatment catalyst composed of one or more metals from group VIB, preferably molybdenum or tungsten, usually associated with one or more metals from group VIII, preferably nickel or cobalt, deposited on an amorphous mineral support, preferably alumina, silica, silica-alumina, magnesia, clays and mixtures of at least two of these elements.

The support may also comprise other compounds, for example, such as oxides selected from the group formed by boron oxide, zirconia, titanium oxide and phosphoric anhydride. The catalyst may be fresh, partially coked or regenerated.

It is possible, for example, to use a catalyst comprising 1% to 10% by weight of nickel, preferably 1% to 5% by weight of nickel (expressed as nickel oxide, NiO) associated with 1% to 30% by weight of molybdenum, preferably 5% to 20% by weight of molybdenum (expressed as molybdenum oxide, $MoO_3$) on an alumina support.

The hydrotreated heavy distillate fraction from selective hydrogenation is cracked with the same cracking catalyst, separately or as a mixture with the heavy hydrocarbon feedstock.

The effluents from catalytically cracking the two feedstocks are sent to a common fractionation zone and the catalyst used for cracking the two feedstocks is regenerated in a common regeneration zone.

As will be disclosed in the next paragraph, the catalytic cracking unit may be classified into a number of modes, with a single reactor processing the heavy hydrocarbon feedstock and the selectively hydrotreated heavy distillate (hydrotreated HCO), or two reactors, one processing the heavy hydrocarbon feedstock, and the other the selectively hydrotreated heavy distillate (hydrotreated HCO).

In addition, each reactor may operate in upflow or downflow mode.

In the case of a plurality of selective hydrotreatment units associated with the catalytic cracking unit, they may be arranged in series or in parallel.

DETAILED DESCRIPTION OF THE INVENTION

According to the invention, the overall feedstock to be cracked contains more than 50% by weight of hydrocarbons with a boiling point of more than 340° C. Generally, the heavy hydrocarbon feedstock treated using FCC is constituted by a vacuum distillate, or possibly an atmospheric residue. The overall cracked feedstock may contain up to 100% by weight of hydrocarbons with a boiling point of more than 340° C.

According to the invention, the cracking catalyst is constituted by a matrix of alumina, silica or silica-alumina with or without an ultra-stable Y type zeolite dispersed in said matrix. Adding an additive based on ZSM-5 zeolite, the quantity of ZSM-5 crystals in the total cracking unit inventory being less than 30% by weight, may also be envisaged.

The catalyst for the selective hydrogenation unit is composed of one or more metals from group VIB, preferably molybdenum or tungsten, usually associated with one or more metals from group VIII, preferably nickel or cobalt, deposited on an amorphous mineral support, preferably alumina, silica, silica-alumina, magnesia, clays or mixtures of at least two of these elements.

The support may also comprise other compounds, for example oxides selected from the group formed by boron oxide, zirconia, titanium oxide and phosphoric anhydride. The catalyst may be fresh, partially coked or regenerated.

As an example, a catalyst comprising 1% to 10% by weight of nickel, preferably 1% to 5% by weight of nickel (expressed as nickel oxide, NiO) associated with 1% to 30% by weight of molybdenum, preferably 5% to 20% by weight of molybdenum (expressed as molybdenum oxide, $MoO_3$) on an alumina support may be used.

The invention can thus be defined as a process for upgrading a heavy distillate cut produced in the FCC unit or any other cut which is rich in triaromatics which cannot be upcycled, by increasing production of the middle distillate cut after recycling to the reaction zone of the FCC while improving the middle distillate to gasoline selectivity and limiting the production of additional coke associated with recycling these triaromatics-rich cuts.

The process of the present invention employs a catalytic cracking unit followed by one or more selective hydrogenation units, in which process the feedstock for the selective hydrogenation unit is constituted by a heavy distillate cut from FCC (denoted HCO), the cut principally being more than 60% constituted by triaromatics, and characterized by a distillation range in the range 320° C. to 490° C., preferably 360° C.-440° C., this cut (LCO) being treated alone or as a mixture with other triaromatics-rich cuts obtained, for example, from visbreaking, coking, "H-oil" type units or the Pygas cut from a steam cracking unit.

Because of the optimized operating conditions for selective hydrogenation, the effluents from the selective hydrogenation unit have a diaromatics to monoaromatics selectivity which is optimized and a proportion of triaromatics which is limited. Minimizing the monoaromatics means that gasoline formation during cracking of this effluent in the catalytic cracking unit is limited, and the transformation of triaromatics into diaromatics can be used to maximize the production of the middle distillate cut in the FCC unit.

Finally, minimizing the triaromatics compounds limits the formation of additional coke linked to cracking of the heavy distillate recycle and as a result has little impact on the thermal balance of the catalytic cracking unit.

The catalytic cracking unit may comprise a single reactor treating both the heavy feedstock and the effluent from the selective hydrogenation unit or two distinct reactors treating on the one hand the heavy feedstock, on the other hand the effluent from the selective hydrogenation unit. In addition, each of the reactors may be in upflow or in downflow mode. Usually, the two reactors will have the same mode of flow.

When the catalytic cracking is carried out in a single reactor in upflow mode, the reactor outlet temperature (ROT) is in the range 450° C. to 650° C., preferably in the range 470° C. to 620° C., and the C/O ratio is in the range 2 to 20, preferably in the range 4 to 15.

When the reactor is in downflow mode, the reactor outlet temperature (ROT) is in the range 480° C. to 650° C., and the C/O ratio is in the range 10 to 50.

When catalytic cracking is carried out in two distinct reactors in upflow mode, the first FCC reactor carrying out cracking of the heavy feedstock operates at a reactor outlet temperature (ROT1) in the range 450° C. to 650° C., preferably in the range 470° C. to 620° C., and with a C/O ratio in the range 2 to 20, preferably in the range 4 to 15. The second FCC reactor carrying out cracking of the selective hydrogenation effluent, i.e. the hydrotreated heavy distillate cut (HCO), operates at a reactor outlet temperature (ROT2) in the range 500° C. to 600° C., preferably in the range 520° C. to 580° C., with a C/O ratio in the range 2 to 20.

When the catalytic cracking is carried out in two distinct FCC reactors in downflow mode, the first FCC reactor carrying out cracking of the heavy feedstock operates at a reactor outlet temperature (ROT1) in the range 480° C. to 650° C. with a C/O ratio in the range 10 to 50.

The second FCC reactor carrying out cracking of the selective hydrogenation effluent, i.e. the hydrotreated heavy distillate cut, operates at a reactor outlet temperature (ROT2) in the range 570° C. to 600° C., with a C/O ratio in the range 10 to 50.

The streams of spent catalyst obtained from the two FCC reactors are separated from the cracking effluents using any gas-solid separation system which is known to the skilled person and regenerated in a common regeneration zone.

The effluent from the catalytic cracking reactor (or the two effluents if there are two FCC reactors) is sent to a fractionation zone to produce a plurality of cuts including a heavy distillate cut with a distillation range in the range 320° C. to 490° C., preferably 360° C. to 440° C., which is then used in the selective hydrogenation unit.

The selective hydrogenation unit is operated at a pressure in the range 15 to 100 bar of hydrogen, preferably 15 to 50 bar, and at a temperature in the range 310° C. to 400° C., preferably in the range 325° C. to 360° C., in the presence of a hydrotreatment catalyst.

The particular conditions of the various steps of the process of the invention will be described hereinafter in more detail.

1) Catalytic Cracking (FCC):

The catalyst for the FCC reactor is typically constituted by particles with a mean diameter generally in the range 40 to 140 micrometer, and usually in the range 50 to 120 micrometer.

The catalytic cracking catalyst contains at least one suitable matrix such as alumina, silica or silica-alumina, with or without the presence of a Y type zeolite dispersed in this matrix.

The catalyst may also comprise at least one zeolite having form selectivity with one of the following structure types: MEL (for example ZSM-11), MFI (for example ZSM-5), NES, EUO, FER, CHA (for example SAPO-34), MFS or MWW. It may also comprise one of the following zeolites: NU-85, NU-86, NU-88 and IM-5, which also have form selectivity.

The advantage of these zeolites with form selectivity is that better propylene/isobutene selectivity is obtained, i.e. a higher propylene/isobutene ratio in the effluents from cracking.

The proportion of zeolite with form selectivity with respect to the total quantity of zeolite may vary as a function of the feedstocks used and of the structure of the desired products. Frequently, 0.1% to 60%, preferably 0.1% to 40% and in particular 0.1% to 30% by weight of zeolite with form selectivity is used.

The zeolite or zeolites may be dispersed in a matrix based on silica, alumina or silica-alumina, the proportion of zeolites (all zeolites together) with respect to the weight of catalyst usually being in the range 0.7% to 80% by weight, preferably in the range 1% to 50% by weight, and more preferably in the range 5% to 40% by weight.

In the case in which a plurality of zeolites is used, they may be incorporated into a single matrix or into a plurality of different matrices. The quantity of zeolite with form selectivity is less than 30% by weight on aggregate.

The catalyst used in the catalytic cracking reactor may be constituted by an ultra-stable Y type zeolite dispersed in a matrix of alumina, silica or silica-alumina, to which an additive based on ZSM-5 zeolite is added, the quantity of crystals of ZSM-5 being less than 30% by weight on aggregate.

The unit for separating the effluents from the catalytic cracking reactor (FCC) generally comprises a primary separation of the FCC effluents in order to allow, inter alia, the production of middle distillate and heavy distillate cuts.

2) Selective Hydrogenation

The aim of this step is to selectively hydrogenate the heavy distillate cut produced in the catalytic cracking unit or any other cut having a high triaromatics content obtained, for example, from visbreaking, coking, "H-oil" type units or the Pygas cut from a steam cracking unit.

Fine-tuning and optimizing the operating conditions of the selective hydrogenation unit means that the majority of the triaromatic compounds can be transformed into diaromatics, thereby limiting the formation of monoaromatics. Because of these optimized operating conditions, the resulting effluent has an increased middle distillate production potential proportional to its diaromatics content at the same time as a limited additional coke and gasoline potential respectively because of the conversion of triaromatics compounds and because of the limitation of monoaromatics compounds.

Selective hydrogenation may be carried out in one or more steps, with one or more reactors arranged in parallel or in series, and one or more catalysts. The following description of a catalyst and the operating conditions may be applied to any one of the steps and/or to any one of the reactors.

The selective hydrogenation catalyst used is preferably a catalyst composed of one or more metals from group VIB, preferably molybdenum or tungsten, usually associated with one or more metals from group VIII, preferably nickel or cobalt, and deposited on an amorphous mineral support, preferably alumina, silica, silica-alumina, magnesia, clays and mixtures of at least two of these elements. The support may also include other compounds, for example oxides selected from the group formed by boron oxide, zirconia, titanium oxide and phosphoric anhydride. The catalyst may be fresh, partially coked or regenerated.

It is possible, for example, to use a catalyst comprising 1% to 10% by weight of nickel, preferably 1% to 5% by weight of nickel (expressed as nickel oxide, NiO) associated with 1% to 30% by weight of molybdenum, preferably 5% to 20% by weight of molybdenum (expressed as the molybdenum oxide, $MoO_3$) on an alumina support.

The operating temperature for selective hydrogenation is in the range 310° C. to 400° C., preferably in the range 325° C. to 360° C.

The operating pressure for selective hydrogenation is in the range 15 bars to 100 bars, preferably in the range 15 bar to 50 bar (1 bar=$10^5$ Pascal).

The invention will now be explained in more detail using the description of FIG. 1.

EXAMPLES

Three examples are provided below to illustrate the improved performances of the process compared with prior art processes.

Example 1 (Prior Art)

Reference Case

The reference case processed a direct HCO recycle without hydrotreatment within the FCC in a dedicated riser.

The HCO composition obtained from cracking a conventional heavy feedstock by FCC is presented in Table 1 ("aro" is the abbreviation for aromatics).

TABLE 1

Composition of ex FCC HCO

|  | Monoaro | Diaro | Triaro+ | Di/mono | SPGR |
|---|---|---|---|---|---|
| ex FCC HCO | 8.1 | 7.7 | 84.1 | 0.949 | 0.957 |

This HCO cut was principally composed of aromatic species 84% by weight of which was triaromatics. The diaromatics to monoaromatics ratio was relatively low, at approximately 1.

This HCO cut, which was subjected to the cracking conditions of a FCC riser, generated the products presented in Table 2. The yields indicated correspond to the yields by weight with respect to the HCO feedstock.

TABLE 2

Yield structure after direct cracking of HCO in FCC

|  | HCO |
|---|---|
| Dry gases | 1.8 |
| LPG | 6.0 |
| LCN | 11.5 |
| HCN | 5.6 |
| Total gasoline | 17.1 |
| LCO | 5.6 |
| HCO | 63.8 |
| Slurry | 2.7 |
| Coke | 3.1 |
| LCO/gasoline | 0.32 |

This direct recycle of HCO was thus able to produce 5.6 additional points of middle distillate and had a selectivity for middle distillate (LCO) over gasoline of 0.32.

Example 2 (Prior Art)

Non-Selective Hydrogenation of HCO

Example 2 considers the case in which the HCO obtained from the FCC unit was sent to a conventional hydrogenation unit under the operating conditions indicated in Table 3:

TABLE 3

Operating conditions for non-selective hydrogenation

| Pressure bar | Temperature ° C. | HSV $h^{-1}$ |
|---|---|---|
| 70 | 335 | 0.5 |

Under these conditions, the cut resulting from this non-selective hydrotreatment had a composition as indicated in Table 4 below ("aro" is the abbreviation for aromatics).

TABLE 4

Composition of HCO after non-selective hydrogenation

|  | Monoaro | Diaro | Triaro+ | Total "aro" | Di/mono | SPGR |
|---|---|---|---|---|---|---|
| Non-selective HDT of HCO | 24.4 | 39.3 | 36.3 | 100 | 1.61 | 0.9831 |

Non-selective hydrotreatment can be used to transform a large portion of the triaromatics into di- and monoaromatics.

Even though the quantity of diaromatics was greatly increased compared with the hydrogenation case, this increase was accompanied by a large increase in monoaromatics.

When cracked in a FCC riser under the same operating conditions as in Example 1, this HCO cut which had been hydrotreated in a non-selective manner resulted in 8 points of middle distillate, i.e. an increase of more than 2 points compared with the case without hydrotreatment, which is highly significant having regard to the tonnages employed in the FCC process.

However, this increase was also accompanied by a great increase in total gasoline, which almost doubled because of the high proportion of monoaromatics in the non-selectively hydrotreated HCO. Thus, the middle distillate selectivity compared with the gas dropped sharply to 0.25.

In a context of greatly minimizing gasoline production, the gain in middle distillate obtained does not compensate for the penalty resulting from an increase in gasoline production.

TABLE 5

Yield structure after direct cracking of HCO hydrotreated non-selectively in FCC, compared with reference case

|  | HCO | Non-selective HDT of HCO |
|---|---|---|
| Dry gases | 1.8 | 1.5 |
| LPG | 6.0 | 7.8 |
| LCN | 11.5 | 21.7 |
| HCN | 5.6 | 10.0 |
| Total gasoline | 17.1 | 31.6 |
| LCO | 5.6 | 8.0 |
| HCO | 63.8 | 47.7 |
| Slurry | 2.7 | 2.0 |
| Coke | 3.1 | 1.4 |
| LCO/gasoline | 0.32 | 0.25 |

Example 3 (in Accordance with the Invention)

Selective Hydrogenation of HCO

Example 3 corresponds to the invention. The HCO resulting from the FCC unit was sent to a selective hydrogenation unit the operating conditions of which had been fixed in order to transform the triaromatics into diaromatics while limiting the production of monoaromatics. The operating conditions under consideration in our study are indicated in Table 6 below:

TABLE 6

Operating conditions for selective hydrogenation

| Pressure bar | Temperature ° C. | HSV h$^{-1}$ | S effluent Wt % |
|---|---|---|---|
| 25 | 335 | 0.5 | 0.255 |

This resulted in a HCO composition after selective hydrogenation which differed from Example 1; this composition is presented in Table 7 below ("aro" is the abbreviation for aromatics):

TABLE 7

Composition of HCO after selective hydrogenation

|  | Monoaro | Diaro | Triaro+ | Total "aro" | Di/mono | SPGR |
|---|---|---|---|---|---|---|
| Selective HDT of HCO | 8.6 | 21.9 | 69.5 | 100 | 2.55 | 0.9818 |

Under the selective hydrogenation conditions, the proportion of diaromatics was of course slightly smaller than in the case of Example 2, but the quantity of monoaromatics was greatly limited. The result was that the ratio of diaromatics to monoaromatics was substantially more favourable at 2.55, as opposed to 1.6 in the case of non-selective hydrogenation.

Thus, a substantial improvement in the selectivity for middle distillate over gasoline can be expected after FCC cracking.

The yields obtained after cracking the selectively hydrogenated HCO are shown in Table 8 below and compared with those obtained in the case of non-selective hydrogenation and direct cracking.

TABLE 8

Yield structure after direct cracking of HCO selectively hydrotreated in FCC compared with reference case and with Example 1

|  | HCO | Non-selective HDT of HCO | Selective HDT of HCO |
|---|---|---|---|
| Dry gases | 1.8 | 1.5 | 1.5 |
| LPG | 6.0 | 7.8 | 5.7 |
| LCN | 11.5 | 21.7 | 13.5 |
| HCN | 5.6 | 10.0 | 7.1 |
| Total gasoline | 17.1 | 31.6 | 20.5 |
| LCO | 5.6 | 8.0 | 7.3 |
| HCO | 63.8 | 47.7 | 60.5 |
| Slurry | 2.7 | 2.0 | 2.4 |
| Coke | 3.1 | 1.4 | 2.0 |
| LCO/gasoline | 0.32 | 0.25 | 0.36 |

As expected, the selectivity for middle distillate over gasoline was very substantially improved at 0.36 when the HCO was selectively hydrogenated. This selectivity was even better than that obtained in the case of a direct recycle of HCO without hydrotreatment.

The gain in middle distillate in the case of selective hydrotreatment of the HCO cut was higher than in the case of a direct recycle of this same cut—7.3 as opposed to 5.6, and slightly smaller than in the case of a non-selective hydrotreatment of the HCO cut.

The major advantage of selective hydrotreatment is at the level of the gasoline cut yield, which remains limited at approximately 20%, and was finally very close to the yield obtained in the case of a direct recycle of the HCO cut.

This gasoline cut yield is also substantially smaller than in the case of non-selective hydrogenation of the HCO cut.

As was the case for non-selective hydrotreatment, the coke from cracking a selectively hydrogenated HCO remains limited and less than in the case of a direct recycle of the HCO cut, which means that the thermal balance of the unit is not perturbed by adding supplemental coke.

This Example 3 clearly illustrates the two aims of the invention, namely:
  upgrading the heavy distillate cut or any cut which is rich in triaromatics, limiting the production of additional coke thereby;

increasing the production of middle distillate at the same time as the selectivity for middle distillate over gasoline.

The invention claimed is:

1. A process for converting a heavy hydrocarbon feedstock having improved selectivity for middle distillate (LCO) with a distillation range in the range 220° C. to 360° C. comprising:
cracking a feedstock using a catalytic cracking unit (FCC) to obtain a heavy distillate cut (HCO), wherein said (HCO) comprises triaromatics in an amount of more than 60% by weight, and has a distillation range of 320° C. to 490° C.,
selectively hydrogenating said HCO with at least one selective hydrogenation unit,
reintroducing said HCO cut into a reaction zone of the FCC unit, wherein the at least one selective hydrogenation unit is operated at a pressure of 15 to 50 bar, and at a temperature of 325° C. to 360° C. and in the presence of a hydrotreatment catalyst comprising 1% to 10% by weight of nickel, associated with 1% to 30% by weight of molybdenum, on an alumina support; and
wherein the catalytic cracking unit (FCC) comprises:
two distinct upflow reactors comprising a first processing of the heavy hydrocarbon feedstock under the following conditions: reactor outlet temperature (ROT1) in the range 450° C. to 650° C., and a C/O ratio in the range 2 to 20 and
a second processing of the hydrotreated heavy distillate cut (HCO) under the following conditions: reactor outlet temperature (ROT2) in the range 500° C. to 600° C., a C/O ratio in the range 2 to 20 and,
wherein the process results in a lower concentration of LPG than HCO.

2. The process for converting a heavy hydrocarbon feedstock having improved selectivity for middle distillate (LCO) according to claim 1, wherein the (HCO) cut obtained from the FCC unit is introduced into the selective hydrogenation unit as a mixture with a cut which is rich in triaromatics.

3. The process of claim 1 wherein the distillation range of the HCO is from 360° C. to 440° C.

4. The process of claim 1 wherein hydrotreatment catalyst comprises 1% to 5% by weight of nickel in the form of nickel oxide.

5. The process of claim 1 wherein hydrotreatment catalyst comprises 5% to 20% by weight of molybdenum in the form of molybdenum oxide.

6. The process of claim 2 wherein the cut is visbreaking, coking, "H-oil" type units or the Pygas cut from a steam cracking unit.

7. The process of claim 1 wherein the reactor outlet temperature (ROT1) range is 470° C. to 620° C. in the first processing and in the C/O ratio range is 4 to 15 in the first processing.

8. The process of claim 1 wherein the reactor outlet temperature (ROT2) range is 520° C. to 580° C. in the second processing.

9. The process of claim 1 wherein the process results in about 5.7% LPG.

10. A process for converting a heavy hydrocarbon feedstock having improved selectivity for middle distillate (LCO) with a distillation range in the range 220° C. to 360° C. comprising:
cracking a feedstock using a catalytic cracking unit (FCC) to obtain a heavy distillate cut (HCO), wherein said (HCO) comprises triaromatics in an amount of more than 60% by weight, and has a distillation range of 320° C. to 490° C.,
selectively hydrogenating said HCO with at least one selective hydrogenation unit,
reintroducing said HCO cut into a reaction zone of the FCC unit, wherein the at least one selective hydrogenation unit is operated at a pressure of 15 to 50 bar, and at a temperature of 325° C. to 360° C. and in the presence of a hydrotreatment catalyst comprising 1% to 10% by weight of nickel, associated with 1% to 30% by weight of molybdenum, on an alumina support; and
wherein the catalytic cracking unit (FCC) comprises:
two distinct upflow reactors comprising a first processing of the heavy hydrocarbon feedstock under the following conditions: reactor outlet temperature (ROT1) in the range 450° C. to 650° C., and a C/O ratio in the range 2 to 20 and
a second processing of the hydrotreated heavy distillate cut (HCO) under the following conditions: reactor outlet temperature (ROT2) in the range 500° C. to 600° C., and a C/O ratio in the range 2 to 20, and
wherein the process results in about 5.7% LPG.

* * * * *